US00PP36600P2

(12) United States Plant Patent
van SWIETEN

(10) Patent No.: US PP36,600 P2
(45) Date of Patent: Apr. 15, 2025

(54) ***PHALAENOPSIS* PLANT NAMED 'PHA925052'**

(50) Latin Name: *Phalaenopsis hybrida*
Varietal Denomination: PHA925052

(71) Applicant: ANTHURA B.V., Bleiswijk (NL)

(72) Inventor: Martinus Nicolaas Gerardus van SWIETEN, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/769,968

(22) Filed: Jul. 11, 2024

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ..... A01H 5/02; A01H 5/00; A01H 6/62
See application file for complete search history.

(56) References Cited

U.S. PATENT DOCUMENTS

PP34,550 P2 * 9/2022 Van Swieten ..... Plt./311

* cited by examiner

*Primary Examiner* — June Hwu
(74) *Attorney, Agent, or Firm* — C. Anne Whealy

(57) ABSTRACT

A new and distinct cultivar of *Phalaenopsis* plant named 'PHA925052', characterized by its upright plant habit; moderately vigorous to vigorous growth habit and moderate growth rate; strong flowering stems; strong leaves; freely flowering habit with typically two inflorescences developing per plant, each inflorescence with numerous flowers; reddish purple-colored flowers with lighter reddish purple-colored petal and sepal margins; and good postproduction longevity.

2 Drawing Sheets

Figure 1:
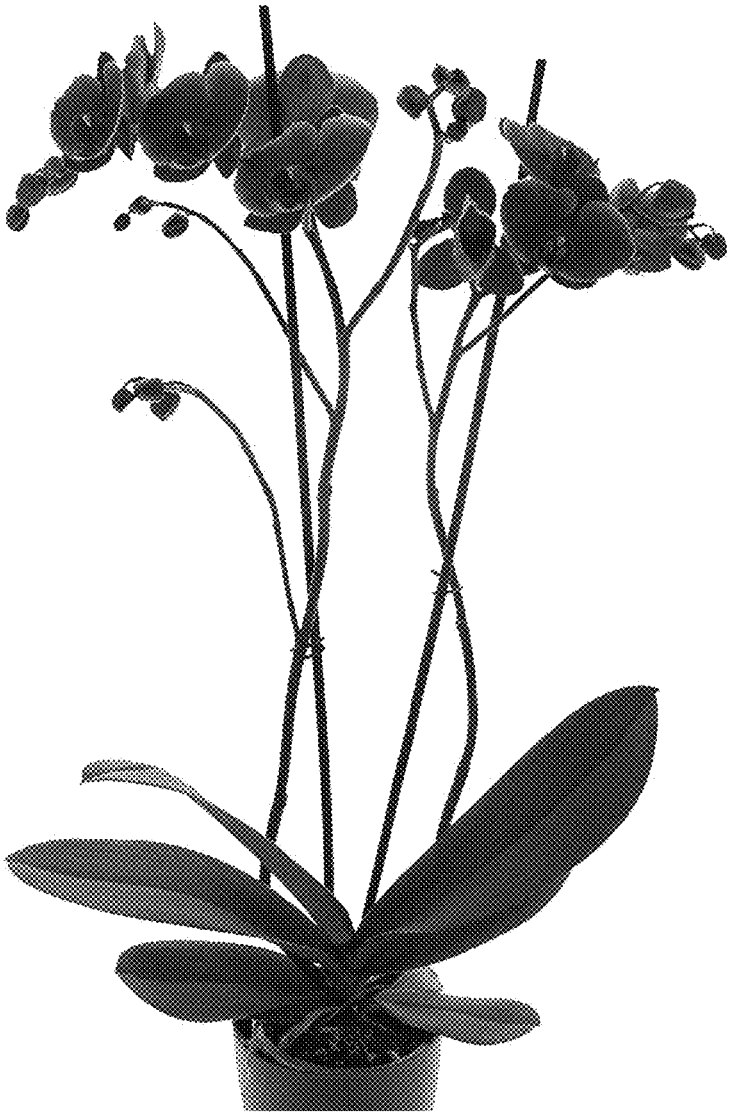

Botanical designation: *Phalaenopsis hybrida.*
Cultivar denomination: 'PHA925052'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Anthura B. V. of Bleiswijk, The Netherlands on Jan. 22, 2023, application number 2023/0206. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'PHA925052'.

The new *Phalaenopsis* plant is a product of a planned breeding program conducted by the Inventor in Bleiswijk, The Netherlands. The objective of the breeding program is to develop new freely flowering *Phalaenopsis* plants with flowers with unique and attractive patterns and coloration.

The new *Phalaenopsis* plant originated from a cross-pollination in September 2016 in Bleiswijk, The Netherlands of *Phalaenopsis hybrida* 'PHALUFREL', disclosed in U.S. Plant Pat. No. 29,259, as the female, or seed, parent with a proprietary selection of *Phalaenopsis hybrida* identified as code number 00001-4992, not patented, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in July 2019.

Asexual reproduction of the new *Phalaenopsis* plant by in vitro meristem propagation in a controlled environment in Bleiswijk, The Netherlands since July 2019 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA925052'. These characteristics in combination distinguish 'PHA925052' as a new and distinct *Phalaenopsis* plant:

1. Upright plant habit.
2. Moderately vigorous to vigorous growth habit and moderate growth rate.

3. Strong flowering stems.
4. Strong leaves.
5. Freely flowering habit with typically two inflorescences developing per plant, each inflorescence with numerous flowers.
6. Reddish purple-colored flowers with lighter reddish purple- colored petal and sepal margins.
7. Good postproduction longevity.

Plants of the new *Phalaenopsis* can be compared to plants of the female parent, 'PHALUFREL'. Plants of the new *Phalaenopsis* differ primarily from plants of 'PHALUFREL' in the following characteristics:

1. Leaves of plants of the new *Phalaenopsis* are horizontal to semi-erect whereas leaves of plants of 'PHALUFREL' are semi-drooping.
2. Petals of plants of the new *Phalaenopsis* are incurving whereas petals of plants of 'PHALUFREL' are flat and not incurving.
3. Petal margins of plants of the new *Phalaenopsis* are not undulate whereas petal margins of plants of 'PHALUFREL' are moderately undulate.

Plants of the new *Phalaenopsis* can be compared to plants of the male parent selection. Plants of the new *Phalaenopsis* differ primarily from plants of the male parent selection in the following characteristics:

1. Leaves of plants of the new *Phalaenopsis* are horizontal to semi-erect whereas leaves of plants of the male parent selection are erect to semi-erect.
2. Dorsal sepals of plants of the new *Phalaenopsis* are longer than dorsal sepals of plants of the male patent selection.

Plants of the new *Phalaenopsis* can be compared to plants of *Phalaenopsis hybrida* 'PHA329179', disclosed in U.S. Plant Pat. No. 34,550. In side-by-side comparisons, plants of the new *Phalaenopsis* differ primarily from plants of 'PHA329179' in the following characteristics:

1. Leaves of plants of the new *Phalaenopsis* are horizontal to semi-erect whereas leaves of plants of 'PHA329179' are semi-erect.
2. Cirrhose tips of plants of the new *Phalaenopsis* are shorter than cirrhose tips of plants of 'PHA329179'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA925052' grown in a container.

Figure 2:
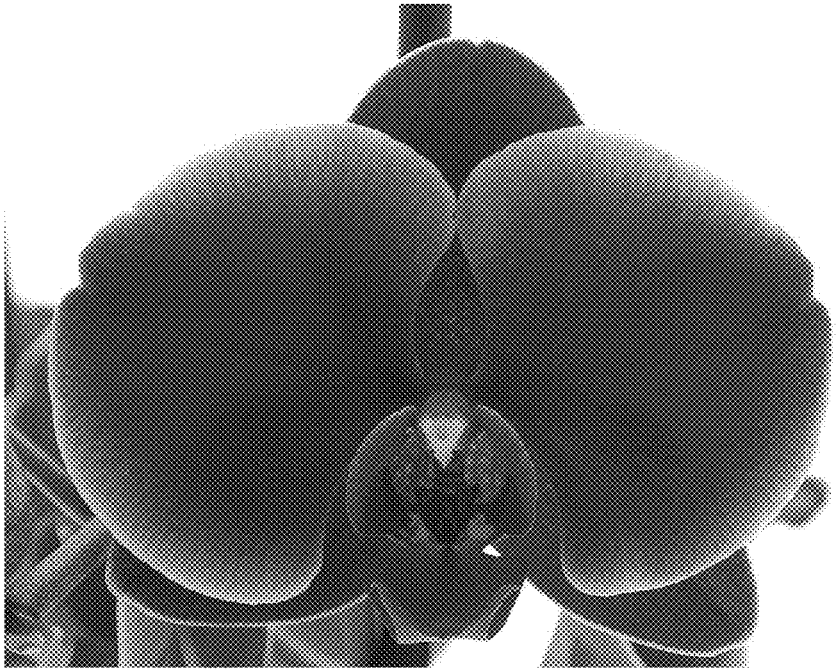

The photograph on the second sheet (FIG. 2) is a close-up view of a typical flower of 'PHA925052'.

DETAILED BOTANICAL DESCRIPTION

The aforementioned photographs and following observations and measurements describe plants grown during the late winter and early spring in 12-cm containers in a glass-covered greenhouse in Bleiswijk, The Netherlands and under cultural practices typically used in commercial *Phalaenopsis* production. Plants were 18 months old when the photographs and description were taken. During the first 14 months of production of the plants, day and night temperatures averaged 28.5° C.; and during the last four months of production of the plants, day and night temperatures averaged 20° C. Throughout the production of the plants, light levels ranged from 100 μmol to 180 μmol. In the following description, color references are made to The Royal Horticultural Society Colour Chart, 2015 Edition, except where general terms of ordinary dictionary significance are used.

Botanical classification: *Phalaenopsis hybrida* 'PHA925052'.

Parentage:

*Female, or seed, parent.*—*Phalaenopsis hybrida* 'PHALUFREL', disclosed in U.S. Plant Pat. No. 29,259.

*Male, or pollen, parent.*—Proprietary selection of *Phalaenopsis hybrida* identified as code number 00001-4992, not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thick, fibrous; typically light green in color; actual color of the roots is dependent on substrate composition, water quality, fertilizer, substrate temperature and age of roots.

*Rooting habit.*—Freely branching; sparse.

Plant description:

*Plant form and growth habit.*—Herbaceous epiphyte; upright plant habit with typically two inflorescences developing per plant, each inflorescence with numerous flowers; monopodial; moderately vigorous to vigorous growth habit and moderate growth rate.

*Plant height, substrate level to top of foliar plane.*—About 21.9 cm.

*Plant height, substrate level to top of floral plane.*—About 57 cm.

*Plant diameter or spread.*—About 31.7 cm.

Leaf description:

*Arrangement and quantity.*—Distichous, simple; sessile; about three to five fully-developed leaves per plant.

*Length.*—About 22.5 cm.

*Width.*—About 7.4 cm.

*Aspect.*—Horizontal to semi-erect.

*Shape.*—Oblanceolate; slightly carinate.

*Apex.*—Unequal acute to unequal broadly acute.

*Base.*—Sheathing. Sheath length: About 1.9 cm. Sheath width: About 1.7 cm. Sheath color: Close to 143B; towards the distal margins, tinged with close to N186C.

*Margin.*—Entire; not undulate.

*Texture and luster, upper and lower surfaces.*—Smooth, glabrous; slightly glossy.

*Venation pattern.*—Camptodromous.

*Color.*—Developing leaves, upper surface: Close to a blend of NN137A and NN137B; towards the margins and apex, close to 187A. Developing leaves, lower surface: Close to a blend of 146A and 147B strongly tinged with close to N186C. Fully expanded leaves, upper surface: Close to NN137B; narrow marginal edges, close to 200A; venation, close to NN137A. Fully expanded leaves, lower surface: Close to a blend of 146B and 147B variably tinged with close to N186C; venation, close to 143A and N186C.

Inflorescence description:

*Appearance and flowering habit*.—Showy zygomorphic flowers arranged on axillary simple or branched racemes; typically two inflorescences develop per plant; each inflorescence with about 19 flowers; flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about four months after planting; plants flower naturally during the winter into the spring.

*Flower longevity*.—Long flowering period, individual inflorescences maintain good substance for about nine weeks on the plant; flowers not persistent.

*Inflorescence length* (*lowermost flower to inflorescence apex*).—About 31.3 cm.

*Inflorescence width*.—About 21.3 cm.

*Flower buds*.—Height: About 2.2 cm. Diameter: About 1.6 cm by 1.9 cm. Shape: Broadly ovate. Color: Close to N79C slightly and variably tinged with close to N77B.

*Flower size*.—About 6.9 cm (vertical) by 8.8 cm (horizontal).

*Flower depth*.—About 3.5 cm.

*Petals, quantity and arrangement*.—Three, two lateral petals and one center petal transformed into a labellum.

*Lateral petals*.—Length: About 4.1 cm. Width: About 5.6 cm. Shape: Reniform. Apex: Shallowly emarginate. Margin: Entire; not undulate. Texture and luster, upper and lower surfaces: Smooth, glabrous, moderately velvety; matte. Color: When opening, upper surface: Close to N79C; towards the margins and apex, close to N78A; towards the base, close to a blend of N79B and N79C. When opening, lower surface: Close to a blend of N78A and N78B; towards the margins and apex, close to N78B; venation, close to N78A. Fully opened, upper surface: Close to NN78A; towards the margins and apex, close to a blend of N78C and N78D; color does not change with subsequent development. Fully opened, lower surface: Close to a blend of N78A and N78B; towards the center, close to NN78C; towards the margins and apex, close to N78C; color does not change with subsequent development.

*Labella*.—Appearance: Three-parted with two lateral lobes and a central lobe. Length, lateral lobes: About 2.3 cm. Width, lateral lobes: About 1.4 cm. Length, central lobe: About 2.5 cm. Width, central lobe: About 9 mm to 20 mm. Length, cirrhose tips: About 7 mm. Shape, lateral lobes: Obovate. Shape, central lobe: Rhomboidal with an elongated apex. Apex, lateral lobes: Obtuse. Apex, central lobe: Cleft with two upwardly and backwardly curled cirrhose tips. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 5 mm in length, about 7 mm in width and about 6 mm in height. Color: When opening, upper surface: Lateral lobes: Close to 187C; towards the apex, close to N80A. Central lobe: Close to 71A; at the base, close to 155A with radial stripes, close to 70A and 71A; main vein close to 61A; cirrhose tips, close to 71A. Callosities: Close to 69C; towards the apex, close 4C and 4D and at the apex, close to 2B; heavily dotted and blotched with close to 183C. When opening, lower surface: Lateral lobes: Close to N78A; towards the base, close to 7A and 198D. Central lobe: Close to 72B; towards the margins and apex, close to N78A; at the base, close to N187D; cirrhose tips, close to N78A. Fully opened, upper surface: Lateral lobes: Close to 187C; towards the apex, close to N80A. Central lobe: Close to 72A; center, close to 71A; at the base, close to 155A with radial stripes and blotches, close to 61A and 72A; main vein close to 71A; cirrhose tips, close to 71A. Callosities: Close to 69C; towards the apex, close 4A and 4B and at the apex, close to 3B; heavily dotted and blotched with close to 183B to 183C. Fully opened, lower surface: Lateral lobes: Close to 72A and 72B; towards the base, close to 71A, 71B and 198D. Central lobe: Close to 72B; towards the margins and apex, close to N78A; at the base, close to N187D; cirrhose tips, close to N78A.

*Sepals*.—Quantity and arrangement: Three, one upper dorsal sepal and two lower lateral sepals. Length, dorsal sepal: About 4.3 cm. Width, dorsal sepal: About 3.4 cm. Length, lateral sepals: About 4.3 cm. Width, lateral sepals: About 2.9 cm. Shape, dorsal sepal: Broadly elliptic. Shape, lateral sepals: Ovate. Apex, dorsal sepal: Obtuse to shallow and minutely emarginate. Apex, lateral sepals: Broadly acute. Base, dorsal and lateral sepals: Truncate. Margins, dorsal and lateral sepals: Entire; not undulate. Texture and luster, dorsal and lateral sepals, upper and lower surfaces: Smooth, glabrous, moderately velvety; matte. Color, dorsal sepal: When opening, upper surface: Close to N79C; narrow marginal edges, close to 76C; fine dots, close to N80D. When opening, lower surface: Close to N79C; towards the margins and apex, close to N79D; narrow marginal edges, close to 76C; fine dots, close to N80D. Fully opened, upper surface: Close to NN78A; narrow marginal edges, close to 76C; fine dots, close to N80D. Fully opened, lower surface: Close to N78B; towards the margins and apex, close to a blend of 77A and 77B; narrow marginal edges, close to 76C; fine dots, close to N80D; venation, close to N78A. Color, lateral sepals: When opening, upper surface: Close to N79C; towards the base, close to 61A and 71A; narrow marginal edges, close to 76C; fine dots, close to N80D. When opening, lower surface: Close to N79C; venation, close to 71A and N79B. Fully opened, upper surface: Close to NN78A; towards the base, close to 71A; narrow marginal edges, close to 76C; fine dots, close to N80D; basal dots and blotches, close to 76C and 76D. Fully opened, lower surface: Close to a blend of N78A and N78B; venation, close to 72A.

*Peduncles*.—Length: About 58.5 cm. Diameter: About 7 mm. Strength: Strong. Aspect: Upright to outwardly arching. Texture and luster: Smooth, glabrous; matte. Color: Close to 200A; heavily dotted with fine dots, close to 147C.

*Pedicels*.—Length: About 3.4 cm. Diameter: About 3 mm. Strength: Moderately strong. Aspect: About 40° from peduncle axis. Texture and luster: Smooth, glabrous; matte. Color: Close to a blend of 71A and N186D; distally, close to 75B and 75C.

*Reproductive organs*.—Androecium: Column length: About 1 cm. Column width: About 6 mm. Column color: Close to NN78A and NN78B. Pollinia quantity: Two. Pollinia diameter (per two pollinia): About 2.5 mm. Pollinia color: Close to 24A. Gynoecium: Stigma length: About 4 mm. Stigma width: About 4.5 mm. Stigma shape: Reniform. Stigma color: Close to 75B. Ovary length: About 8 mm. Ovary diameter: About 1 mm. Ovary color: Close to 149C.

Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA925052' as herein illustrated and described.

* * * * *